United States Patent
Lee et al.

(10) Patent No.: US 6,818,778 B2
(45) Date of Patent: Nov. 16, 2004

(54) PROCESS FOR PREPARING (-)-(18-CROWN-6)-2,3,11,12-TETRACARBOXYLIC ACID, AND (-)-CHIRAL STATIONARY PHASES FOR RESOLUTION OF RACEMIC COMPOUNDS USING THE SAME

(75) Inventors: Ho Seong Lee, Daejeon (KR); Chang Soo Lee, Daejeon (KR); Jin Won Yun, Choongcheong-bookdo (KR); Seong Jin Kim, Daejeon (KR); Kyung-Hyun Gahm, Daejeon (KR)

(73) Assignee: Rstech Co., Ltd. (KR)

( * ) Notice: Subject to any disclaimer, the term of this patent is extended or adjusted under 35 U.S.C. 154(b) by 0 days.

(21) Appl. No.: 10/432,326

(22) PCT Filed: Nov. 12, 2001

(86) PCT No.: PCT/KR01/01926

§ 371 (c)(1),
(2), (4) Date: May 22, 2003

(87) PCT Pub. No.: WO02/42288

PCT Pub. Date: May 30, 2002

(65) Prior Publication Data

US 2004/0044231 A1 Mar. 4, 2004

(30) Foreign Application Priority Data

Nov. 23, 2000 (KR) ......................... 2000-70104

(51) Int. Cl.$^7$ ............................................ C07D 323/00
(52) U.S. Cl. ........................................................ 549/214
(58) Field of Search ......................................... 549/214

(56) References Cited

PUBLICATIONS

Chyuch et al., Fresenius J. Ana. Chem. (1996), vol. 354, pp. 278–283.*

* cited by examiner

Primary Examiner—Taofiq Solola
(74) Attorney, Agent, or Firm—Finnegan, Henderson, Farabow, Garrett & Dunner, L.L.P.

(57) ABSTRACT

The present invention relates to a process for preparing (–)-(18-crown-6)-2,3,11,12-tetracarboxylic acid and its use for (–)-chiral stationary phases for resolution of racemic compounds. More particularly, the present invention relates to the process for preparing (–)-(18-crown-6)-2,3,11,12-tetracarboxylic acid expressed by formula (1) and the use thereof as a stationary phases for resolution of racemic compounds, wherein the use of them provides excellent separation of a desired chiral compound from racemic mixture in employing capillary electrophoresis (CE) or liquid chromatography to elute the desired one first by controlling a flowing order of enantioners, thus allowing to be consistently separated in an economical due to much less requirement of eluent, quantitative and high purity manner.

5 Claims, No Drawings

PROCESS FOR PREPARING (-)-(18-CROWN-6)-2,3,11,12-TETRACARBOXYLIC ACID, AND (-)-CHIRAL STATIONARY PHASES FOR RESOLUTION OF RACEMIC COMPOUNDS USING THE SAME

This Application is a 317 of PCT/KR01/01926 filed Nov. 12, 2001.

FIELD OF THE INVENTION

The present invention relates to a process for preparing (-)-(18-crown-6)-2,3,11,12-tetracarboxylic acid and its use for (-)-chiral stationary phases for resolution of racemic compounds. More particularly, the present invention relates to the process for preparing (-)-(18-crown-6)-2,3,11,12-tetracarboxylic acid expressed by the following formula (1) and the use thereof as a stationary phases for resolution of racemic compounds, wherein the use of this stationary phase provides excellent separation of a desired chiral compound from racemic mixture in employing capillary electrophoresis (CE) or liquid chromatography (LC) to elute the desired one first by controlling a flowing order of enantiomers, thus allowing to be consistently separated in an economical due to much less requirement of eluent, quantitative and high purity manner,

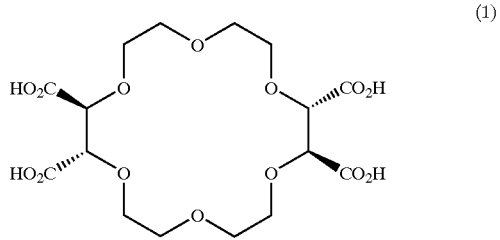

(1)

wherein the compound of formula (1) is an enantiomer which has not been reported for its preparation processes and uses.

On the other hand, (+)-isomer, (+)-(18-crown-6)-2,3,11,12-tetracarboxylic acid, of the compound of formula (1) has been synthesized by Hiroyuki Nishi et al. and used for separation of enantiomers from racemic mixtures (*Journal of Chromatography A*, 757, 1997, 225-235). Hiroyuki Nishi et al. have used said enantiomer as a stationary phase of capillary electrophoresis or liquid chromatography to separate out a desired chiral compound from racemic mixture which was unresolvable or difficult to resolve previously. This is particularly useful for the separation of amino compounds.

Further, Yoshio Machida et al. have developed (+)-chiral stationary phase for liquid chromatography by immobilizing (+)-(18-crown-6)-2,3,11,12-tetracarboxylic acid on the surface of silica gel to separate enantiomers which was unresolvable or difficult to resolve previously (*Journal of Chromatography A*, 805, 1998, 85–92).

Recently, Myung Ho Hyun et al. have developed a chiral stationary phase for liquid chromatography prepared by a different method immobilizing (+)-(18-crown-6)-2,3,11,12-tetracarboxylic acid to silica gel to employ in resolving various racemic mixtures (Korea Patent No. 262872; *Journal of Chromatography A*, 822, 1998, 155–161; *Journal of Chromatography A*, 837, 1999, 75–82; *Bull. Korean Chem. Soc.* 1998, Vol. 19, No. 8, 819–821).

In addition, it has been reported for resolution of racemic mixtures having amino acid or amine functional groups using (+)-(18-crown-6)-2,3,11,12-tetracarboxylic acid in *Journal of Chromatography A*, 680, (1994) 253–261; *Journal of Chromatography A*, 685, (1994) 321–329; *Anal. Chem.* 1996, 68, 2361–2365; *Journal of Chromatography A*, 810 (1998) 33–41; *Journal of Chromatography A*, 666 (1994) 367–373; *Electrophoresis* 1994, 15, 828–834; *Journal of Chromatography A*, 709 (1995) 81–88; *Chromatographia* Vol. 49, No. 11/12, (1999) 621–627; *Chromatographia* Vol. 33, No. 1/2, (1992) 32–36; *Anal. Chem.* 1992, 64, 2815–2820; *Journal of Chromatography A*, 716 (1995) 371–379; *Journal of Chromatography A*, 715 (1995) 143–149; *Journal of Chromatography A*, 757 (1997) 328–332; *Electrophoresis* 1999, 20, 2650–2655; *Electrophoresis* 1999, 20, 2605–2613.

Particular examples of amino compounds or drugs which exist in chiral mixtures include tyrosine, phenylglycilne, 2-amino-1-phenylethanol, normetanephrine, norephedrine, alanine-beta-naphthylamide, quinolone derivatives and the like. These optically pure chiral compound separated from the racemic mixture have been possible for quantitative analysis.

However, in these days, technologies such as simulated moving bed (SMB) technology for efficient separation of optically pure compounds directly from racemic mixtures in high yield and large scales are highly increased not only for quantitative analysis but also for the development the pharmaceutical and fine chemical industries (*Chemical & Engineering New*, 2000, Jun. 19). Development of novel chiral stationary phases for production chiral drugs becomes significant.

In the process to obtain each enatiomer from racemic mixture in high yield and purity, first fractions are usually pure chiral compound but later fractions are incomplete separation of the components. Thus, it may result poor separation and low purity and yield for especially later flowing chiral compound. Particularly, in the process to determine accurate purity of chiral compound via quantitative analysis, if a major chiral compound elutes first and a minor chiral one does later, it becomes difficult to determine an accurate purity of later flowing compound due to tailing effect of the first fractions. It is general that flowing concentration per unit time is lower and flowing time takes longer for the later flowing compound than the first flowing one.

However, certain pharmaceutical compounds, known to provide effective treatment against disease states or to ameliorate medical conditions, often occur as a chiral mixture where one enantiomeric form has the desired therapeutic activity whereas the other enantiomeric form of the same compound causes undesirable side-effects and may limit drug efficacy. Therefore, it is highly beneficial to be able to separate out and collect the most effective forms of enantiomeric compounds.

Since FDA's (Food and Drug Administration's) Policy Statement revised in 1992 for Development of New Drugs reported that each isomer of the same compound having the same structure is regarded as a different compound and side effects associated with undesired isomer in the human body have often reported, chiral separation with high yield and purity has become more and more important in pharmaceutical and fine chemical fields.

As a result, the demand in the development of capillary electrophoresis, LC chiral column, and simulated moving bed technologies to increase separation efficiency has been rapidly increased in recent years. A separation efficiency may be increased by controlling a flowing order of chiral compounds to be separated. This flowing order in the SMB technology has a significant influence on relative difficulty of the process, purity of the separated compound, cost and the like.

Inventors have applied ASTEC's Cyclobond™, Chirobiotic™ V, T, and R columns which is based on bonding α-, β- or γ-cyclodextrin, or vancomycin to silica gel to separate various chiral compounds. However, the process is inefficient because it requires too complicate process and much efforts, even though it provides well separation of each enantiomer.

In the process to separate (R) and (S)-isomer and determine accurate purity thereof by employing capillary electrophoresis or LC chiral stationary phase column, if the first flowing fractions are major and the later ones are minor, the first flowing ones can be eluted with some of the later flowing ones due to tailing effect of the first flowing ones, thus it becomes difficult to obtain accurate optical purity. In this case, if the minor compound can be eluted first and major one later, it can avoid tailing effect of the major compound, thus allowing to determine an accurate optical purity of the minor compound. Even though there is tailing effect of the minor compound, the tailing effect associated with the minor compound must be much smaller than that with the major one or can be ignored, thus it does not affect to determine accurate optical purities. In case that the large scale chiral separation is performed by using SMB column or LC chiral stationary phase column, it will be preferable to elute a desired chiral compound first to avoid tailing effect of the later flowing compound, further provides several advantages in reducing amount of eluent, performing process and the processing time. Further, the control of the flowing order allows more accurate optical purity.

SUMMARY OF THE INVENTION

The inventors have completed the present invention by providing a process for preparing (−)-(18-crown-6)-2,3,11,12-tetracarboxylic acid and its use for (−)-chiral stationary phases for resolution of racemic compounds to control flowing order in the chiral separation using capillary electrophoresis or LC chiral column and producing the optically pure compound effectively.

Accordingly, an object of the present invention is to provide a process for preparing (−)-(18-crown-6)-2,3,11,12-tetracarboxylic acid. Another object is to provide its use for (−)-chiral stationary phases for resolution of racemic compounds and preparation thereof. Further object is to provide its use in capillary electrophoresis.

DETAILED DESCRIPTION OF THE INVENTION

The present invention provides a process for preparing (−)-(18-crown-6)-2,3,11,12-tetracarboxylic acid of formula (1) to be used for resolution of racemic compounds.

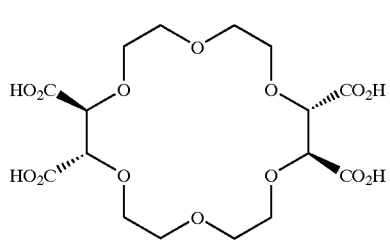

(1)

The present invention also provides (−)-chiral stationary phases of formula (2) for LC chiral column and manufacturing method thereof,

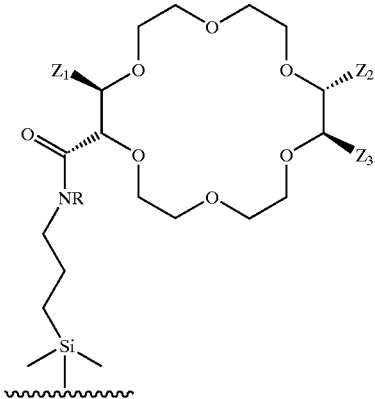

(2)

wherein R represents a hydrogen atom or $C_1$–$C_4$ low alkyl group; each of $Z_1$, $Z_2$, and $Z_3$ represents $CO_2H$ or a complex of formula (3) bonded with silica gel,

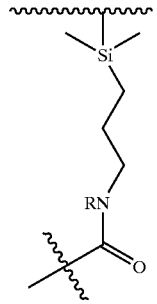

(3)

wherein R is same as defined previously.

The present invention will be discussed in more detail hereunder.

(+)-(18-crown-6)-2,3,11,12-tetracarboxylic acid has been utilized as a capillary electrophoresis or chiral stationary phase by liquid chromatography (HPLC) as described above in the prior art. On the other hand, (−)-(18-crown-6)-2,3,11,12-tetracarboxylic acid of formula (1) of the present invention is a different compound from the known isomer, (+)-(18-crown-6)-2,3,11,12-tetracarboxylic acid, and has different utilities. For example, in order to obtain (R)-isomers of amino acids, which do not naturally exist, by chiral separation SMB method or (−)-chiral stationary phase column unlike (+)-(18-crown-6)-2,3,11,12-tetracarboxylic acid is used to elute (R)-isomer first, thus providing several advantages in avoiding to reduce optical purity of (R)-isomer, shortening the chiral separation process with saving time, and reduction in cost.

As shown in Scheme 1, (−)-(18-crown-6)-2,3,11,12-tetracarboxylic acid of formula (1) is prepared by hydrolysis of octaethyl (−)-(18-crown-6)-2,3,11,12-tetracarboxamide of formula (6) obtained by condensation of N,N,N',N'-tetraalkyl-D-tartaramide of formula (4) with the compound of formula (5), Scheme 1

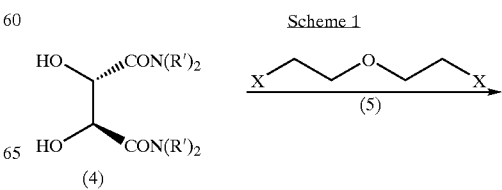

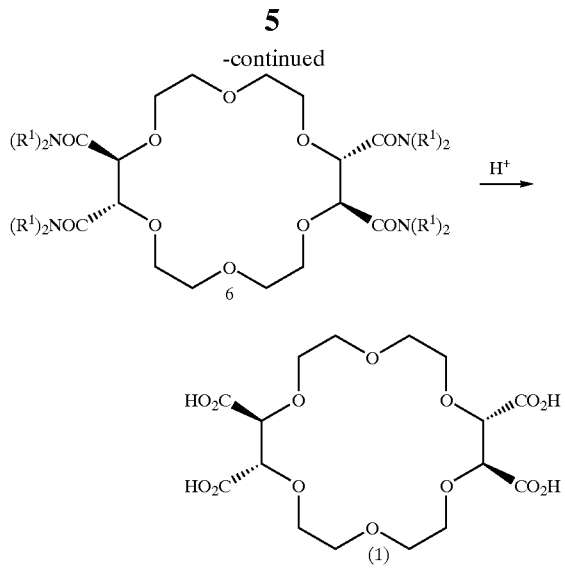

wherein R' represents $C_1$–$C_4$ low alkyl; X represents Cl, Br, I, p-toluenesulfoxide(TsO) or methanesulfoxide(MsO).

N,N,N',N'-Tetraalkyl-D-tartaramide of formula (4) dissolved in an organic solvent chosen from dimethylformamide, dimethylacetamide, and tetrahydrofuran is reacted with a base chosen from sodium hydride, thallium ethoxide, and potassium t-butoxide. 1–20 Equivalents of the compound of formula (5) is added and condensed at 50–100° C. to produce octaethyl (−)-(18-crown-6)-2,3,11,12-tetracarboxamide of formula (6). The obtained octaethyl (−)-(18-crown-6)-2,3,11,12-tetracarboxamide of formula (6) is hydrolyzed in acidic solution at 50–100° C. to produce (−)-(18-crown-6)-2,3,11,12-tetracarboxylic acid of formula (1).

The present invention further provides a (−)-chiral stationary phase for liquid chromatography using (−)-(18-crown-6)-23,11,12-tetracarboxylic acid of formula (1) and a process for preparing the same. (−)-Chiral stationary phase is prepare by converting (−)-(18-crown-6)-2,3,11,12-tefracarboxylic acid of formula (1) to the corresponding anhydride of formula (7) and then condensing the result with aminopropyl silica gel or monoalkylaminopropyl silica gel, or by condensing the result directly with aminopropyl silica gel or monoalkylaminopropyl silica gel using a binding agent, wherein each of R, $Z_1$, $Z_2$ and $Z_3$ are same as defined previously.

In Scheme 2, (−)-(18-crown-6)-2,3,11,12-tetracarboxylic acid of formula (1) is treated with acetyl chloride or acetic anhydride, thionyl chloride, phosphorus oxychloride without using any organic solvent; with 2,2'-dipyridyl disulfide or 4,4'-dipyridyl disulfide in the presence of trialkylphosphine or triphenylphosphine in an organic solvent chosen from dichloromethane, dichloroethane, acetone, toluene, benzene, ether and ethyl acetate; or with phosphorus pentachloride in the same solvent system to produce the corresponding anhydride of formula (7). The obtained anhydride of formula (7) is condensed with aminopropyl silica gel or monoalkylaminopropyl silica gel in the presence of triethylamine or pyridine in an organic solvent chosen from dichloromethane, dichloroethane, toluene, and benzene to produce (−)-chiral stationary phase of formula (2).

And also (−)-chiral stationary phase of formula (2) may be prepared by condensing (−)-(18-crown-6)-2,3,11,12-tetracarboxylic acid of formula (1) with aminopropyl silica gel or monoalkylaminopropyl silica gel in the presence of 2 equivalents of 1,3-dicyclohexylcarbodiimide or N-ethoxycarbonyl-2-ethoxy-1,2-dihydroquiloline as a binding agent in an organic solvent chosen from dichloromethane, dichloroethane, acetone, toluene, benzene, ether and ethyl acetate.

The (−)-chiral stationary phase of formula (2) is suspended in methanol and the slurry is charged in HPLC column using slurry charger to produce (−)-chiral column.

The following examples and experimental examples are intended to further illustrate the present invention without limiting its scope.

EXAMPLE 1

Preparation of Octamethyl (−)-(18-crown-6)-2,3,11,12-tetracarboxamide

N,N,N',N',-tetramethyl-D-tartaramide (35 g) was added regularly in sodium hydride (8.02 g, 95%) in dimethylformamide under $N_2$, while stirring at 0° C. After the reaction mixture was further stirred at room temperature for 1 hour, di(ethylene glycol)di-p-tosylate (71.05 g) dissolved in dimethylformamide was added to it. After performing the reaction at 80° C. for 8 hours, dimethylformamide was removed under the pressure. The residue was triturated with chloroform and the precipitate was filtered out. The filtrate was evaporated under the pressure and the residue was purified Scheme 2

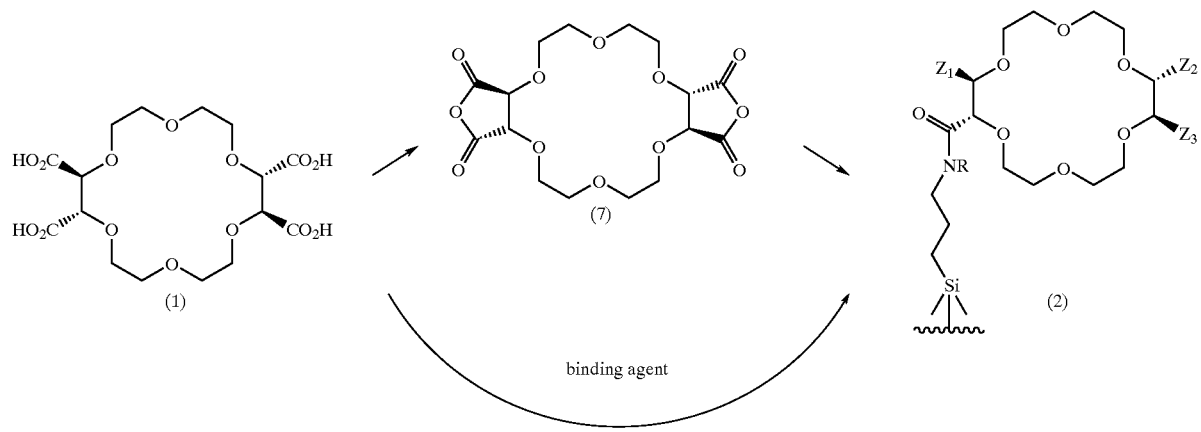

by column chromatography on alumina by eluting with dichloromethane to yield the desired product (6.5 g).

$^1$H NMR(CDCl$_3$) δ(ppm): 2.92(s, 12H), 3.16(s, 12H), 3.65–3.96(m, 16H), 4.80(s, 4H); [a]$_D$=−110°(c=1.5, CHCl$_3$)

EXAMPLE 2

Preparation of Octamethyl (−)-(18-crown-6)-2,3,11,12-tetracarboxamide

Thallium ethoxide (42.5 g) was added regularly into N,N,N',N',-tetramethyl-D-tartaramide (17.5 g) in dimethylformamide under N$_2$, while stirring at 0° C. After the reaction mixture was further stirred at room temperature for 1 hour, bromoethyl ether (200 g) was added to it. After performing the reaction at 80° C. for 8 hours, dimethylformamide and excess bromoethyl ether were removed under the pressure. The residue was dissolved in dichloromethane, washed with water, and evaporated under the pressure. The residue was purified by column chromatography on alumina by eluting with dichloromethane. The obtained fractions were evaporated and the result was dissolved in dimethylformamide. In another flask, thallium ethoxide (21.2 g) was added regularly into N,N,N',N',-tetramethyl-D-tartaramide (8.8 g) in dimethylformamide under N$_2$, while stirring at 0° C. After the reaction mixture was further stirred at room temperature for 1 hour, the obtained compound previously dissolved in small amount of dimethylformamide was added to the reaction mixture. After performing the reaction at 80° C. for 8 hours, dimethylformamide was removed under the pressure. The residue was triturated with chloroform and the precipitate was filtered out. The filtrate was evaporated under the pressure and the residue was purified by column chromatography on alumina by eluting with dichloromethane to yield the desired product (6.0 g).

$^1$H NMR(CDCl$_3$) δ(ppm): 2.92(s, 12H), 3.16(s, 12H), 3.65–3.96(m, 16H), 4.80(s,4); [a]$_D$=−108°(c=1.5, CHCl$_3$)

EXAMPLE 3

Preparation of (−)-(18-crown-6)-2,3,11,12-tetracarboxylic Acid 2.5N of hydrochloride solution (60 mL) was added to octamethyl (−)-(18-crown-6)-2,3,11,12-tetracarboxamide (6 g) and the mixture was stirred at 80° C. for 24 hours. The reaction mixture was evaporated under the pressure and the residue was past through an ion exchange resin by using water. Water was evaporated and the residue was crystallized using minimum amount of water to yield the desired product (3.9 g).

$^1$H NMR(CD$_3$OD) δ(ppm): 3.63–3.91(m, 16H), 4.65(s, 4H); [α]$_D$=−63°(c=1, MeOH)

EXAMPLE 4

Preparation of (−)-(18-crown-6)-2,3,11,12-tetracarboxylic anhydride

Acetyl chloride (24 mL) was added to (−)-(18-crown-6)-2,3,11,12-tetracarboxylic acid (969 mg) under N$_2$ and the reaction mixture was heated at reflux for 18 hours. Excess acetyl chloride was evaporated under the pressure to yield the desired product (890 mg).

$^1$H NMR(CDCl$_3$) δ(ppm): 3.62–4.17(m, 16H), 4.83(s, 4H)

EXAMPLE 5

Preparation of (−)-chiral Stationary Phase (Compound 2; R=H)

Dichloromethane (33 mL) and triethyl amine (0.77 mL) were added to aminopropyl silica gel (8.08 g) under N$_2$. (−)-(18-Crown-6)-2,3,11,12-tetracarboxylic anhydride, obtained in Example 4, dissolved in dichloromethane (17 mL) was added to the reaction mixture at 0° C. The reaction mixture was stirred at room temperature for 24 hours, filtered, washed with methanol, water, methanol, dichloromethane, and hexane in series and dried to yield the desired product (8.8 g).

EXAMPLE 6

Preparation of (−)-chiral Stationary Phase (Compound 2; R=Me)

(−)-Chiral stationary phase was prepared by the same procedure as that of Example 5, excepting using monomethylaminopropyl silica gel instead of aminopropyl silica gel to yield the desired product (8.8 g).

EXAMPLE 7

Preparation of (−)-chiral Stationary Phase (Compound 2; R=H)

To a mixture of (−)-(18-crown-6)-2,3,11,12-tetracarboxylic anhydride (969 mg), 1,3-dicyclohexylcarbodiimide (908 mg) and aminopropyl silica gel (8.08 g) was added benzene (33 mL). The reaction mixture was heated at reflux for 4 hours, filtered, washed with methanol, water, methanol, dichloromethane, and hexane in series and dried to yield the desired product (8.8 g).

EXAMPLE 8

Preparation of (−)-chiral Stationary Phase (Compound 2; R=Me)

(−)-Chiral stationary phase was prepared by the same procedure as that of Example 7, excepting using monomethylaminopropyl silica gel instead of aminopropyl silica gel to yield the desired product (8.8 g).

Experimental Example 1

Chiral separation by (−)-chiral column IC charged with (−)-chiral stationary phase (compound 2; R =H)

The (−)-chiral stationary phase (2.5 g) prepared in Example 5 was suspended in methanol (20 mL) and charged into HPLC column (150 mm ×4.6 mm I.D.) by using slurry charger to produce (−)-chiral column. Separation of the following pounds in Table 1 was performed by using the prepared (−)-chiral column with eluent of methanol/water =80/20 and sulfuric acid (10 mM) under the condition of low rate of 0.5 mL/min (1.2 mL/min for quinolone A and B), detector of 210 nm UV (294 m for quinolone A and B), and a temperature of 20° C. The result was compared with that performed the (+)-chiral stationary phase liquid chromatography prepared by using (+)-(18-crown-6)-2,3,11,12-tetracarboxylic acid and summarized in Table 1.

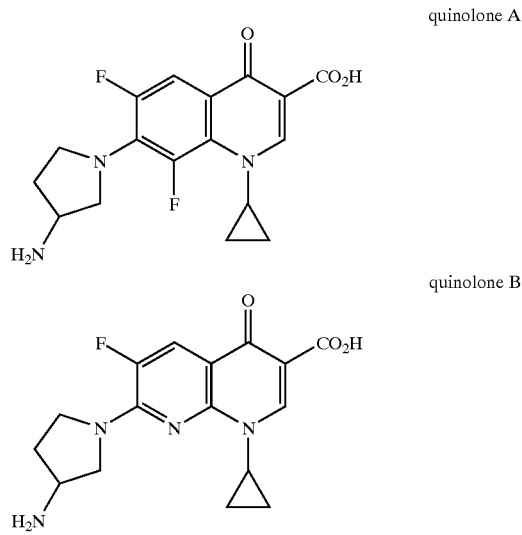

quinolone A quinolone B

TABLE 1

| Racemic compound | (−)-chiral column | | | | (+)-chiral column | | | |
| --- | --- | --- | --- | --- | --- | --- | --- | --- |
| | First fraction | | Second fraction | | First fraction | | Second fraction | |
| | Capacity factor k1 | Absolute configuration | Capacity factor k2 | Absolute configuration | Capacity factor k1 | Absolute configuration | Capacity factor k2 | Absolute configuration |
| Alanine | 1.36 | R | 1.76 | S | 1.37 | S | 1.76 | R |
| Tyrosine | 0.85 | R | 1.21 | S | 0.84 | S | 1.21 | R |
| Threonine | 0.24 | 2S, 3R | 0.35 | 2R, 3S | 0.24 | 2R, 3S | 0.34 | 2S, 3R |
| Tocainide | 1.91 | R | 2.21 | S | 1.90 | S | 2.22 | R |
| 1-Aminoindane | 1.17 | S | 1.80 | R | 1.16 | R | 1.79 | S |
| 2-Phenylglycinol | 1.43 | R | 1.95 | S | 1.44 | S | 1.95 | R |
| Qunolone A | 9.50 | R | 10.95 | S | 9.50 | S | 10.94 | R |
| Qunolone B | 14.02 | R | 14.74 | S | 14.01 | S | 14.76 | R |

Experimental Example 2

Chiral Separation by (−)-chiral Column LC Charged with (−)-chiral Stationary Phase (Compound 2; R=Me)

The (−)-chiral stationary phase (2.5 g) prepared in Example 6 was suspended in methanol (20 mL) and the slurry was charged into HPLC column (150 mm×4.6 mm I. D.) by using slurry charger to produce (−)-chiral column. Separation of the following compounds in Table 2 was performed by using the prepared (−)-chiral column with eluent of methanol/water=80/20 and sulfuric acid (10 mM) under the condition of flow rate of 1.2 mL/min, detector of 210 nm UV (294 nm UV for quinolone B), and a temperature of 20° C. The result was compared with that performed with (+)-chiral stationary phase liquid chromatography prepared by using (+)-(18-crown-6)-2,3,11,12-tetracarboxylic acid and summarized in Table 2.

Experimental Example 3

Chiral Separation by (−)-chiral Column LC Charged with (−)-chiral Stationary Phase (Compound 2; R=H)

Separation of the following compounds in Table 3 was performed by using the prepared (−)-chiral column charged with (−)-chiral stationary phase (compound 2; R=H) with eluent of methanol/water=80/20 and sulfuric acid (10 mM) under the condition of flow rate of 1 mL/min (2 mL/min for quinolone 1 and 2), detector of 210 nm UV (294 nm for quinolone 2), and a temperature of 20° C. The result was compared with that performed with (+)-chiral stationary phase liquid chromatography prepared by using (+)-(18-crown-6)-2,3,11,12-tetracarboxylic acid and summarized in Table 3.

TABLE 2

| Racemic compound | (−)-chiral column | | | | (+)-chiral column | | | |
| --- | --- | --- | --- | --- | --- | --- | --- | --- |
| | First fraction | | Second fraction | | First fraction | | Second fraction | |
| | Capacity factor k1 | Absolute configuration | Capacity factor k2 | Absolute configuration | Capacity factor k1 | Absolute configuration | Capacity factor k2 | Absolute configuration |
| Leucine | 5.98 | R | 7.42 | S | 5.99 | S | 7.43 | R |
| Phenylglycine | 11.13 | R | 19.61 | S | 11.14 | S | 19.61 | R |
| Tocainide | 1.52 | R | 1.81 | S | 1.52 | S | 1.82 | R |
| 1-Aminoindane | 8.31 | S | 20.13 | R | 8.32 | R | 20.13 | S |
| 2-Phenylglycinol | 14.71 | R | 17.94 | S | 14.70 | S | 17.93 | R |
| Qunolone B | 12.80 | R | 20.94 | S | 12.81 | S | 20.92 | R |

TABLE 3

| Racemic compound | (−)-chiral column | | | (+)-chiral column | | |
| --- | --- | --- | --- | --- | --- | --- |
| | Yield (mg) | Optical purity (% ee) | Absolute configuration | Yield (mg) | Optical purity (% ee) | Absolute configuration |
| Tyrosine | 9.7 | >99.9 | R | 7.3 | 99.7 | R |
| 1-Aminoindane | 9.7 | >99.9 | S | 7.4 | 99.7 | S |
| 2-Phenylglycinol | 9.7 | >99.9 | R | 7.1 | 98.8 | R |
| Qunoline A | 9.3 | 99.8 | R | 5.5 | 98.0 | R |

Experimental Example 4
Chiral Separation by (−)-chiral Column LC Charged with (−)-chiral Stationary Phase (Compound 2; R=Me)

Separation of the following compounds in Table 4 was performed by using the prepared (−)-chiral column charged with (−)-chiral stationary phase (compound 2; R=Me) with eluent of methanol/water=80/20 and sulfuric acid (10 mM) under the condition of flow rate of 2.5 mL/min, detector of 210 nm UV (294 nm UV for quinolone 1), temperature of 20° C. The result was compared with that performed with (+)-chiral stationary phase liquid chromatography prepared by using (+)-(18-crown-6)-2,3,11,12-tetracarboxylic acid and summarized in Table 4.

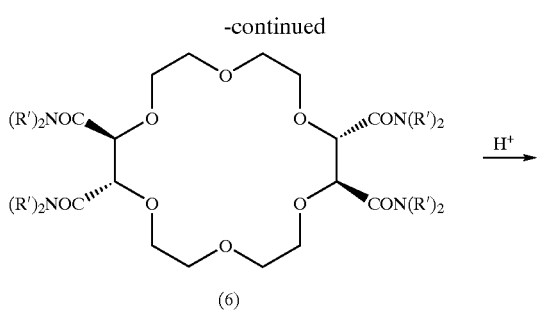

TABLE 4

| Racemic compound | (−)-chiral column | | | | (+)-chiral column | | | |
| --- | --- | --- | --- | --- | --- | --- | --- | --- |
| | Yield (mg) | Yield (%) | Optical purity (% ee) | Absolute configuration | Yield (mg) | Yield (%) | Optical purity (% ee) | Absolute configuration |
| Tyrosine | 9.7 | 97 | >99.9 | R | 8.2 | 82 | 99.0 | R |
| 1-Aminoindane | 9.9 | 99 | >99.9 | S | 9.7 | 97 | 99.8 | S |
| 2-Phenylglycinol | 9.7 | 97 | >99.9 | R | 8.5 | 85 | 98.8 | R |
| Qunolone B | 9.9 | 99 | 99.8 | R | 9.7 | 97 | 99.5 | R |

As shown the above Examples and Experimental Examples, it is noted that the present invention provides uses of (−)-(18-crown-6)-2,3,11,12-tetracarboxylic acid of formula (1) in chiral separation by capillary electrophoresis and (−)-chiral stationary phase for liquid chromatography. The present invention further provides excellent separation efficiency in high yield and high purity by eluting the desired chiral compound first, and allows determining accurate optical purity thereof.

What is claimed is:

1. A process for preparing (−)-(18-crown-6)-2,3,11,12-tetracarboxylic acid of formula (1) by hydrolysis of octaethyl (−)-(18-crown-6)-2,3,11,12-tetracarboxamide of formula (6) obtained by condensation of N,N,N',N'-tetraalkyl-D-tartaramide of formula (4) with the compound of formula (5),

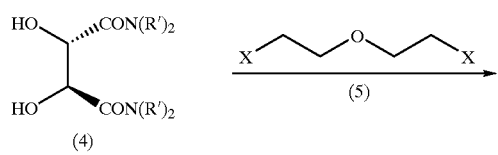

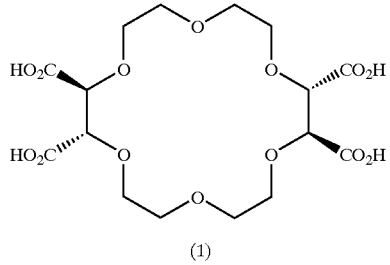

wherein R' represents $C_1$–$C_4$ low alkyl; X represents Cl, Br, I, p-toluenesulfoxide(TsO) or methanesulfoxide(MsO).

2. A (−)-chiral stationary phase of formula (2) for liquid chromatography for resolution of chiral compound from racemic mixtures,

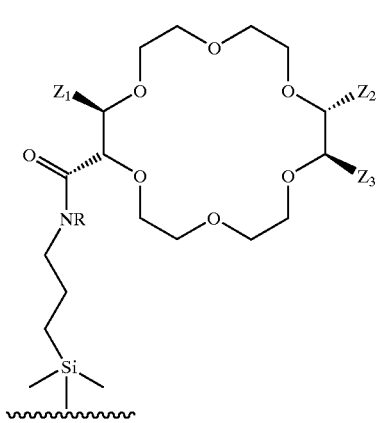

(2)

wherein R represents a hydrogen atom or $C_1$–$C_4$ low alkyl group; each of $Z_1$, $Z_2$, and $Z_3$ represents $CO_2H$ or a complex of formula (3) bonded with silica gel,

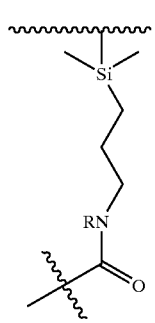

(3)

wherein R is same as defined previously.

3. A process for preparing (−)-chiral stationary phase of formula (2) by converting (−)-(18-crown-6)-2,3,11,12-tetracarboxylic acid of formula (1) to the corresponding anhydride of formula (7) and condensing the result with aminopropyl silica gel or monoalkylaminopropyl silica gel,

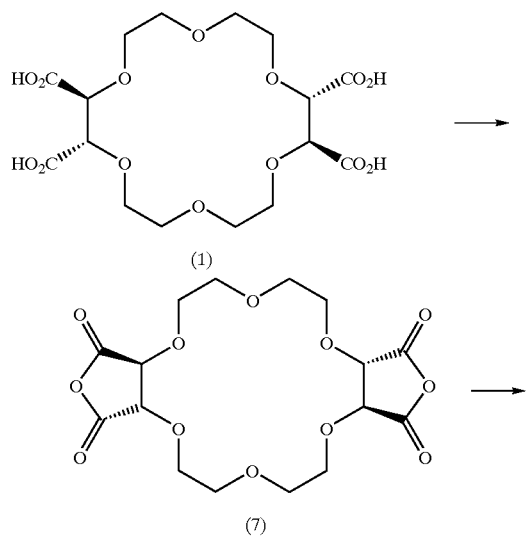

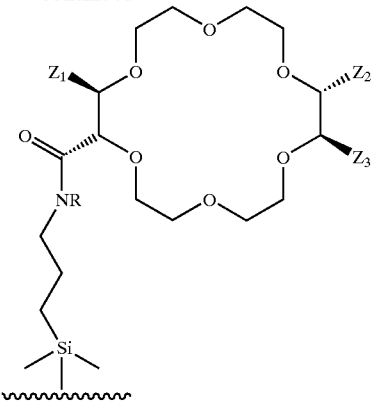

(2)

wherein R represents a hydrogen atom or $C_1$–$C_4$ low alkyl group; each of $Z_1$, $Z_2$ and $Z_3$ represents $CO_2H$ or a complex of formula (3) bonded with silica gel.

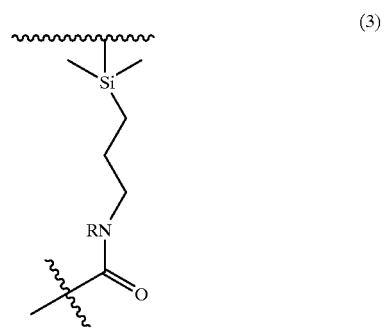

(3)

wherein R is same as defined previously.

4. A process for preparing (−)-chiral stationary phase of formula (2) by condensing (−)-(18-crown-6)-2,3,11,12-tetracarboxylic acid of formula (1) with aminopropyl silica gel or monoalkylaminopropyl silica gel using a binding agent,

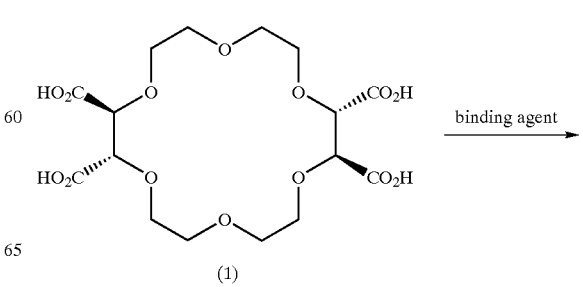

-continued

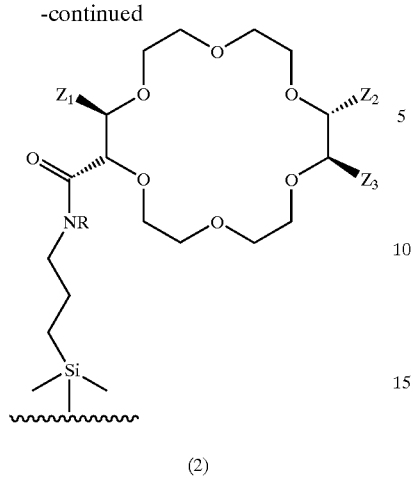

(2)

wherein R represents a hydrogen atom or $C_1$–$C_4$ low alkyl group; each of $Z_1$, $Z_2$, and $Z_3$ represents $CO_2H$ or a complex of formula (3) bonded with silica gel,

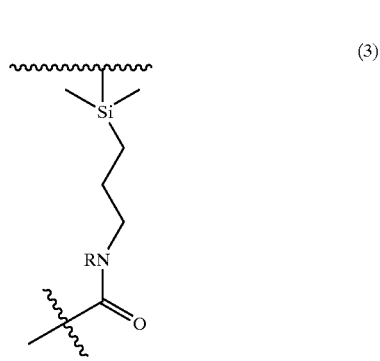

(3)

wherein R is same as defined previously.

5. A (−)-chiral column for liquid chromatography prepared by using (−)-chiral stationary phase of formula (2),

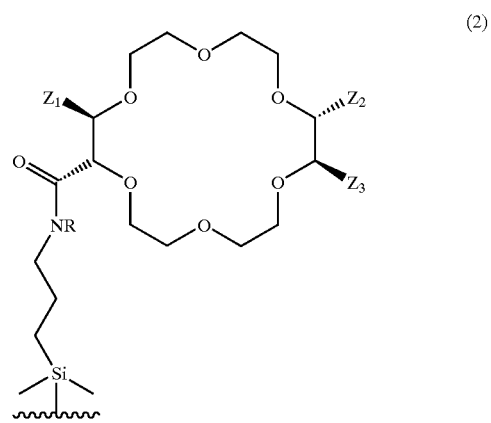

(2)

wherein R represents a hydrogen atom or $C_1$–$C_4$ low alkyl group; each of $Z_1$, $Z_2$, and $Z_3$ represents $CO_2H$ or a complex of formula (3) bonded with silica gel,

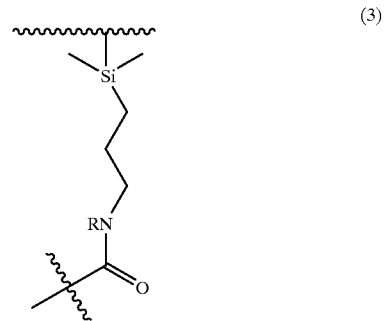

(3)

wherein R is same as defined previously.

* * * * *

UNITED STATES PATENT AND TRADEMARK OFFICE
CERTIFICATE OF CORRECTION

PATENT NO. : 6,818,778 B2
DATED : November 16, 2004
INVENTOR(S) : Ho Seong Lee et al.

It is certified that error appears in the above-identified patent and that said Letters Patent is hereby corrected as shown below:

Title page,
Item [57], ABSTRACT,
Line 7, "phases" should read -- phase --.
Line 12, "enantioners" should read -- enantiomers --.

Column 14,
Line 25, "gel." should read -- gel, --

Signed and Sealed this

Fifth Day of April, 2005

JON W. DUDAS
*Director of the United States Patent and Trademark Office*